United States Patent [19]

Rump et al.

[11] Patent Number: 5,725,425
[45] Date of Patent: Mar. 10, 1998

[54] SENSOR SYSTEM FOR CONTROLLING VENTILATION SYSTEMS IN VEHICLES

[75] Inventors: Hanns Rump, Unna-Massen; Norbert Pieper, Selm; Jörg Hiller, Wetter; Olaf Kiesewetter, Geschwenda, all of Germany

[73] Assignee: Auto Electronics Corporation, Seoul, Rep. of Korea

[21] Appl. No.: 700,398

[22] PCT Filed: Apr. 6, 1995

[86] PCT No.: PCT/KR95/00033

§ 371 Date: Aug. 29, 1996

§ 102(e) Date: Aug. 29, 1996

[87] PCT Pub. No.: WO95/29435

PCT Pub. Date: Nov. 2, 1995

[30] Foreign Application Priority Data

Apr. 27, 1994 [DE] Germany ............... 44 14 594.2
Oct. 15, 1994 [DE] Germany ............... 44 36 938.7

[51] Int. Cl.⁶ .................. B61D 27/00; E21B 43/00
[52] U.S. Cl. .................. 454/75; 454/229; 165/249; 73/23.31
[58] Field of Search .................. 454/75, 99, 229; 165/249; 73/23.31, 31.02

[56] References Cited

U.S. PATENT DOCUMENTS

| | | | |
|---|---|---|---|
| 4,437,391 | 3/1984 | Eguchi et al. | 364/424 |
| 4,992,965 | 2/1991 | Holter et al. | 454/75 X |
| 5,252,949 | 10/1993 | Kirby et al. | 73/23.31 X |
| 5,320,577 | 6/1994 | Tooru et al. | 454/75 |

FOREIGN PATENT DOCUMENTS 4312046  10/1994  Germany .................. B60H 1/00

*Primary Examiner*—William E. Wayner
*Attorney, Agent, or Firm*—Robert E. Malm

[57] ABSTRACT

A motor vehicle ventilation system having a recirculation or air input mode in which when the rate of change of a signal from an outdoor gas pollution sensor exceeds a threshold limit, the system is adjusted to the recirculation mode.

39 Claims, 11 Drawing Sheets

SENSOR SYSTEM FOR CONTROLLING VENTILATION SYSTEMS IN VEHICLES

TECHNICAL FIELD

The invention centers on a sensor system which controls the ventilation systems in vehicles, both for incoming air and recirculation mode, depending on the concentration of poisonous fumes in the atmosphere outside the vehicle, using a gas sensor element, the electrical resistance of which falls in case of reducing gases and which rises when oxidizing gases are present, together with an evaluation unit, the output of which is connected to the controls of the ventilation system.

BACKGROUND ART

It is known that by using gas sensor elements, for example tin dioxide elements, the presence of oxidable gases can be registered, for example the presence of carbon monoxide, hydrocarbons and hydrogen. During the process, a gas-sensitive layer within the gas sensor element, which can consist of conductive and heated tin dioxide, might be reduced by the oxidable gas; thus a reduction of the ohmic resistance of the gas-sensitive tin dioxide layer in the gas sensor element occurs. Such gas sensor elements are included in sensor systems which control ventilation systems in vehicles. Whenever the vehicle in question enters an area with a high concentration of poisonous fumes, the ventilation system will be switched to recirculation operation, ensuring that the fumes are kept out of the interior of the vehicle.

The usual sensor systems, especially those fitted with tin dioxide sensor elements, react to a very limited extent only to diesel exhaust emissions, although diesel emissions disturb vehicle passengers subjectively more than many petrol emissions, such as carbon monoxide, since these fumes may not be smelled as obviously as diesel emission fumes. The reason for this behavior lies in a masking effect which occurs, because diesel emissions contain not only oxidable gases, but also high levels of nitric oxide, which are gases which may be reduced and are thus oxidizing gases. The nitric oxide contained in the diesel emissions once again oxidises the gas sensitive tin dioxide layer of the gas sensor element, which has been reduced by the oxidable gases contained in the diesel emissions, so that the reducing and oxidizing effects created by the charging of the gas sensitive tin dioxide layer cancel each other out to a great extent.

For an explanation of the 'Masking Effect', see FIGS. 1-3. FIG. 1 shows a sensor circuit, which demonstrates a heated gas sensor element 1 and an external resistor 2. The external resistor 2 can also be replaced by a constant electrical source. The divider current UM measured between the heated gas sensor element 1 and the external resistor 2 is a function of the gas-altered ohmic resistance of heated gas sensor element 1.

FIG. 2 shows the change in the ohmic resistance in gas sensor element 1, when coated only with reducing gases or only with oxidizing gases. Impulse 3 shown in the figure is the result of gas sensor element contact with gases that can be oxidized, for example with carbon monoxide (CO). Impulse 4 is the result of gas sensor element 1 contact with gases that can be reduced, for example with nitric oxide (NOx).

FIG. 3 shows the 'Masking Effect', impulse 5 occurs through gas sensor element contact with reducing carbon monoxide that can be oxidized. In FIG. 3, impulse 5 is followed by impulse 6, which is achieved by a mixture of carbon monoxide and nitric oxide. In spite of the presence of nitric oxide in the mixture, the ohmic resistance of the gas sensor element remains lower than in the uncoated state. In spite of the presence of reducible and thus oxidizing nitric oxides in diesel exhaust emissions, the ohmic resistance of gas sensor element 1 remains under the level that it would have in an emission-free state. The effect occurs because of the oxidable and thus reducing gases which are present in diesel emissions. Under extreme conditions, the ohmic resistance of the gas sensor element 1 can show the same level following contact with mixed gas that would be reached by gas sensor element contact to fresh air. In any case, the value of the gas sensor signal given following contact by gas sensor element 1 with mixed gas is considerably reduced, since in the extreme case demonstrated above the gas sensor signal does not differentiate between contact by gas sensor element 1 with mixed gas and gas sensor element contact with fresh air.

Since simply detected oxidable and reducing gases lower the ohmic level of the tin dioxide layer of the gas sensor element, and reducible and oxidizing gases raise the ohmic level of the tin dioxide layer of the gas sensor element, it had always been assumed that in order to ensure accurate control of ventilation systems in vehicles that two gas sensor elements would be required. In this way, one gas sensor element serves to measure gases that can be oxidized and are thus reducing, whilst the other gas sensor element serves to detect reducible and thus oxidizing gases.

Sensor systems for controlling vehicle ventilation systems which are equipped with two gas sensor elements are comparatively complicated. This is primarily due to the fact that two gas sensor elements are present. Furthermore, the gas sensor signals produced by both of these gas sensor elements have to be processed and then linked to each other in such a way as to allow evaluation, which means a comparatively complicated organization of the processing and evaluation unit.

DISCLOSURE OF INVENTION

The invention results from the task of developing a sensor system to control ventilation systems in vehicles, both for incoming air and recirculation more, connected to the concentration of hazardous fumes in the atmosphere outside the vehicle, through which the sensor tasking and the evaluation thereof may be carried out more simply and in a less complicated manner.

The task for the sensor system which was explained above has been solved by the invention of a sensor system that is so organized that, the increase of a gas sensor signal fed into the evaluation unit following an increase in the concentration of reducing gases, which amounts approximately to the fall of the gas sensor signals fed into the evaluation unit for an appropriate increase in the concentration of oxidizing gases. The system also ensures that the evaluation unit can measure the rise and fall of the gas sensor signals per unit of time, and that the evaluation unit transmits a switching signal to alter the operation of the ventilation system to recirculation mode as soon as the calculated rise and or fall of the gas sensor signals per time unit exceeds a predetermined limit.

The organization of the sensor system uses the fact that within normal ventilation systems for vehicles impulsive occurrence of air pollution through various substances must be expected, and that static conditions in the atmosphere around the vehicle will not be found, since the vehicle itself will be moving. Furthermore, the sensor system envisaged by the invention uses the typical reaction of a gas sensor element, that is to say that the gas sensor element coated with a gas typically reacts relatively quickly in the adsorption phase, whereby the reverse phase, during which the gas sensor element once again reaches its original state, takes three to five times longer. The presence of a gas concentration in the atmosphere around the vehicle will be recognized and the ventilation system of the vehicle will be switched to recirculation mode, when the rise or fall of the gas sensor element signals per time unit exceeds a predetermined limit. It is not important whether the gas sensor signal rises or falls, since the degree of the rise or fall will be measured and compared to the predetermined limit. Should the limit be exceeded, a switch signal will be generated, to switch the ventilation system into recirculation mode.

In order to be certain that a switch signal will only be generated to switch the ventilation system into recirculation mode when a measurable degree of pollution is present in the air, and in order to avoid unnecessarily frequent switching of the ventilation system, it is advantageous to ensure that the switch signal is only then generated when the calculated rise and or fall of the gas sensor signal compared to the limit, actually takes place over a predeterminable period of time.

In order to ensure that the air inside the vehicle retains a certain quality despite a slow build-up of pollution, as opposed to sudden concentrations of fumes, it is of advantage for the evaluation unit to calculate a mean value for the gas sensor signal, measured over a given period of time, whereby the mean value is added to, or subtracted from an absolute value and then placed within a defined limit band, so that the switch signal is produced when the gas sensor signal lies outside the limits of the band.

The switching behavior of the ventilation system intended by the invention is feasible with comparatively little complication, if the evaluation unit has a band range which only allows a frequency band to pass which indicates a rising or falling value for the gas sensor signal per time unit that exceeds the given limit, over which the gas sensor signal is conducted, in order to detect such a rise and or fall of the gas sensor signal per time unit, the signal of which will be used to produce the switch signal to control the ventilation system.

Furthermore, the switch function required by the invention is also feasible if the evaluation unit is fitted with a computer to carry out a Fourier transformation, whereby the gas sensor signals are examined to discover whether or not a certain frequency band is present, indicating that the limit has been exceeded by rising or falling gas sensor signals per time unit, with the switch signal for the control of the ventilation system being generated in the evaluation unit should such a frequency band be detected in the gas sensor signal.

A further advantageous example of the invention becomes apparent when the evaluation unit is fitted with an electronic neural network, in which the gas sensor signal is examined for logical characteristics to see if a rise or fall in the gas sensor signal per time unit is exceeding the set limit, whereby a switch signal will be generated in the evaluation unit, should a value from a rise or fall in the gas sensor signal that exceeds the set limits be detected during the examination.

It is possible that the electronic neural network be constructed in the form of a triple or multiple-layer forward coupled neural network. Thus not only current, but also previously measured gas sensor signals (or signals calculated from these gas sensor signals) could be used as an input value. The output of this neural network provides the necessary signals to control the ventilation system.

As an alternative to a triple or multiple-layer forward coupled neural network, a triple or multiple-layer backward coupled neural network may be fitted.

Furthermore, it is possible to describe the switch behavior required by the invention in logical rules. The evaluation unit can then be fitted with an electronic fuzzy logic unit, which can be measured by means of the rise or fall of the gas sensor signal per time unit which exceeds the present limit, whereby the switch signal is generated in the evaluation unit when the rise or fall of the gas sensor signal exceeds the preset limit in the course of the examination.

For practical purposes the evaluation unit is so designed that the switch signal stops when the gas sensor signal lies inside the hand formed by the constructed mean values and no amplitude spectrum is detected in the rise or fall of the gas sensor signal which exceeds the preset limits. In this way, it may he ensured that the ventilation system of the vehicle in question always functions in recirculation mode when the level of the air pollution in the atmosphere around the vehicle is unacceptably high and when an unacceptably steep rise in pollution in the air around the vehicle is detected.

It is extremely important that the return of the switch signal to stop the operation of recirculation mode, or a switch signal to restart input of air be generated at a defined point in time, from which time on the quality of the air outside the vehicle may be considered acceptable. In this respect, several methods have been suggested, not all of which lead to acceptable results. As an example for the current state of the art technology, the method should he described with which the size of the gas contact to a gas sensor element is the value for the operational period of the ventilation system in recirculation mode. Here it is unfavorable that due to a short-term pollution of the air, that may be for example produced at a traffic light, a comparatively long operational period of the ventilation system in recirculation mode follows, which is completely unnecessary, especially when the vehicle in question overtakes the source of the pollution, for example another vehicle, following the stop at the traffic light. On the other hand, in highly polluted tunnels, the situation described above leads to the ventilation system being switched to recirculation mode due to the high level of pollutants in the atmosphere, whereby the system may come to the end of the set operational period, dependent on the air around the vehicle, and could under certain circumstances switch the system back to air input in the middle of the tunnel. In this way the interior of the vehicle will be supplied with a high level of polluted air.

In order to avoid such a reaction by the ventilation system, the evaluation unit has been fitted with a data storage facility in which the peaks of the gas sensor signals are stored, whereby in output the evaluation unit deactivates the switch signal if the gas sensor signal does not show a certain predeterminable signal difference from one peak to the next and the gas sensor signal is within the hand for the formed mean value.

It is of utmost importance for the practical requirements of the invented sensor system to control vehicle ventilation systems that the reactive sensitivity of the sensor system be adjusted to the driving situation and the given environment. At this point the capability of the human nose should be taken into account, since it too is capable of adjusting itself to changing pollutant concentrations in the atmosphere. The invented sensor system should thus react extremely sensitively to detected pollutants in areas with mostly unpolluted clean air, whilst the reactive sensitivity of the invented sensor system must be reduced when the vehicle is mostly being driven in areas where the pollutant level of the outside atmosphere and the frequency of peak levels of harmful substances is very high. Such an alteration of the reactive sensitivity is absolutely necessary to achieve a relation between ventilator operational time in recirculation mode and ventilator operational time in air input mode, in order that, even under driving conditions where the outside atmosphere is highly polluted, the ventilation system runs for no more than 50% of the given time in recirculation mode. Only in this way can the reliable removal of passenger-produced moisture and scents from the vehicle interior be ensured. This method of operation also avoids the occurrence of falling oxygen levels within the vehicle which could be caused by an extended period of ventilator operation in recirculation mode, and which could also be damaging to passenger health. Assuming that the interior of the vehicle has a volume of 2 cubic meters and that the vehicle is fully occupied, a rule applies that the oxygen content in the air may not fall below 20%; thus if the occupants of the vehicle are breathing normally, the ventilation system has a maximum operating period of 15 minutes in recirculation mode. Without an automatic alteration in the reactive sensitivity dependent on the current traffic situation, the operation of a sensor system is not always satisfactory. A further influence, Stems from the fact that the gas sensor elements in sensor systems can demonstrate a wide range of tolerances with respect to their specific sensitivity, within the range +/−3. Furthermore, gas sensor elements can alter their sensitivity following exposure to certain gaseous substances within their operating life-span. The exposure conditions for gas sensor elements can also be altered by the construction components positioned near to the gas sensor elements. It should also always be taken into account that atmospheric pollution may be divided into base impurities, which may for example be foremost in a town or region, and the occurrent peak pollutants, produced by vehicles preceding the vehicle in question. The base pollution will normally be lower in rural or suburban areas than in heavy traffic zones in inner city urban areas.

To compensate for the influences listed above, and to compensate for their unwanted effects on the gas sensor element, it is suggested in one advantage version of the invention that the evaluation unit should have a regulator to alter the reactive sensitivity of the sensor system, under which the reactive sensitivity of the sensor system may be increased or decreased according to whether the frequency of the gas sensor signals which exceed the preset limit measured over a period of time is rising or falling, whereby the number of alterations in the reactive sensitivity of the sensor system per unit of time is limited.

Such a variability of the reactive sensitivity of the sensor system can be set up relatively simply, if the evaluation unit is fitted with a time measurement unit for measuring the operational periods of the ventilation system in air input and recirculation mode, a computer unit for calculating the quotient of operational periods of the ventilation system in air input and recirculation mode, and a regulator to reduce the reactive sensitivity of the sensor system when recirculation mode operation increases and to increase the reactive sensitivity of the sensor system when air input operation is increased, whereby the number of alterations in the reactive sensitivity of the sensor system is limited over a given period of time.

In a further advantageous model of the invention with variable reactive sensitivity, the regulator unit is fitted with outside temperature sensor, (which measures the temperature outside the vehicle), an internal temperature sensor, (which measures the temperature inside the vehicle), together with a comparison unit which compares the outside air temperature, measured by the outside temperature sensor unit, with the internal air temperature, as measured by the internal air sensor unit, whereby the regulator increases or decreases the reactive sensitivity of the sensor system when the outside air temperature is higher or lower than the internal air temperature.

The evaluation unit with the task of controlling the ventilation system can take the form of a centrally-programmed microprocessor or be analogically technical.

The gas sensor element used in the invented sensor system can be a metal dioxide gas sensor element. It should be taken into account that the usual tin dioxide gas sensor elements are so constructed that their reactive sensitivity towards oxidable gas is particularly high, whilst their reactive sensitivity to reducible gases is very low. To be able to use such a metal dioxide gas sensor element within the framework of the invented sensor system, it must be so fitted that it is more or less equally sensitive to both oxidable and reducible gases. With most of the current state of the art technology sensor systems, this means that these sensor systems are especially susceptible to the type of masking effect already described above. On the other hand, metal dioxide gas sensor elements which are equally sensitive to both oxidable and reducible gases can be used advantageously in the case of the invented sensor system, since in this case the degree of rise and or fall of the gas sensor signal is numerically measured.

Whilst fitting the gas sensor elements for the invented sensor system it became obvious that basically nearly all current state of the art technology metal oxide gas sensor elements, including tin dioxide gas sensor elements, reduce their electrical resistance when coated with oxidable gases, and increase their electrical resistance when coated with reducible gases. The relation required by the invented sensor system with regard to sensitivity cannot be provided by current state of the art technology metal oxide gas sensor elements and tin dioxide gas sensor elements, since when the gas sensor element comes into contact with diesel emission fumes the amounts range from 100 to 200 ppb (parts per billion) and by contact with petrol emission fumes from 1 to 50 ppm (parts per million).

For application in the invented gas sensor system, the gas sensor element is constructed as a mixed oxide sensor element, the gas-sensitive layer consists of tin dioxide ($SnO_2$), tungsten trioxide ($WO_3$), ferric oxide ($Fe_2O_3$), aluminium oxide ($Al_2O_3$) with platinum (Pt) and palladium (Pd) as reaction accelerators.

The mixed oxide sensor element has particularly advantageous characteristics when the gas-sensitive layer has the following proportions; 29–49%, preferable approximately 39% tin dioxide ($SnO_2$), 7–13%, preferably 10% ferric oxide ($Fe_2O_3$), 28–48%, preferably 38% tungsten trioxide ($Wo_3$), 7–13%, preferably 10% aluminum oxide ($Al_2O_3$), 1–3%, preferably 2% palladium (Pd), and 0.5–1.5%, preferably 1% platinum (Pt). It should however be noted that other combinations are possible, by means of which a comparable reactive sensitivity may be reached for contact with diesel or petrol emission fumes.

The gas sensor element can be mounted directly on an electrical circuit board and connected with the circuit board by means of precious metal wires.

In one advantageous version of the system the gas sensor element is contacted with platinum wire and mounted in an opening of an electrical circuit board of the evaluation unit at approximately the same level, with gas sensor element connections soldered directly onto the circuit board, so that the gas sensor element is freely mounted.

Metal oxide gas sensor elements alter their characteristics when the temperature on the surface sensor element changes. When used in the sensor system, the metal oxide gas sensor elements and therefore the surface of the sensor elements are exposed to the external atmosphere. This situation produces the problem that high speed driving may cause the direct air contact on the surface of the sensor element to create a strong cooling effect.

The suggested solution to the problem was to fit the metal oxide gas sensor element with a labyrinth, which would be so designed as to allow the outside air to reach the metal oxide gas sensor element, but at the same time to sufficiently protect the metal oxide gas sensor element against moisture, impurities, dirt particles and air currents.

The disadvantage of such a construction would be that, because of the long way needed for the outside air to travel through the labyrinth, the reactive sensitivity speed of the metal oxide gas sensor element would be slowed down and that various gases would adsorb on the comparatively large surface area of the labyrinth.

The solution to the problem was found in the current state of the art technology, namely to place the gas sensor element behind gas-permeable barriers, whereby the barriers allow the gas unlimited access to the metal oxide gas sensor element, whilst at the same time ensuring that the sensor has enough protection against moisture, impurities, dirt particles and air currents.

Such gas-permeable barriers are normally in the form of mounted membranes, which as long as they are subject to air movements may be brought to vibrate in this way air movements may be created in the area directly around metal oxide gas sensor element, leading to an alteration of the temperature on the surface of the sensor element. The metal oxide gas sensor element reacts to such changes in its surface temperature by altering its electrical resistance, so that the gas sensor signal is unacceptably overlaid by this distortion factor.

In order to avoid such distortion factors which may render evaluation of the gas sensor signal more difficult, the invention version of the sensor system calls for the gas sensor element to be fitted in a gas-tight chamber which is in turn fitted opposite the evaluation unit. The chamber has a low volume, is of stable form and has gas-permeable walls. In this way the required rapid reactive sensitivity of the gas sensor element can be reached, since on the one hand the volume of the chamber in which the gas sensor element is placed is as limited as possible, whilst on the other hand unwanted air movements within the chamber will not occur, due to the stable formation of the walls.

The walls of the chamber may be partially at least constructed of perforated material, which can hold and mechanically support at least one layer of the gas-permeable plastic without deformation. It is additionally possible to place at least one layer of the gas-permeable plastic between two layers of metal webbing.

Instead of placing the gas-permeable plastic between metal webbing, it may be bedded between two stable sections of perforated thermoplastic material.

It is of advantage if at least one layer of the gas-permeable plastic is constructed of plastic film.

As long as the plastic film is constructed of teflon or some similar substance, then it can be ensured that gas, for example carbon monoxide or nitric oxide, diffuses through the plastic film due to gas pressure difference, without an actual air transport having taken place. One other alternative form would be feasible, whereby the stable gas-permeable walls of the chamber housing the gas sensor element are formed of sintered plastic, glass, metal or similar materials. Such sintered forms, according to their material, possess a surface that makes them more or less watertight, but still allow the passage of gases.

It is additionally of advantage for the reactive sensitivity of the gas sensor element if the chamber housing the gas sensor element is hemispherical.

The fitting of the gas sensor element in a chamber with the characteristics described above means that the reaction time of the gas sensor element to a change in the pollutant level in the outside atmosphere is also minimized as a result of the fact that the space surrounding the gas sensor element is also minimized. Thus the gas sensor element is also well protected against air movements, dust, moisture, water, wax and other aerosols which are used in the motor industry and maintenance operations. Furthermore, the use of such a chamber form allows a low cost, comparatively inexpensive construction.

Many of the application forms of the invented sensor system can benefit from having the gas sensor element and the evaluation unit in one single housing.

If in this case a form is selected, by which the gas sensor element and a part unit of the evaluation unit are combined in one sensor module, the part unit of the evaluation unit has an oscillating circuit, a capacitor to measure the frequency of the oscillating circuit and a heating regulator to control the temperature of the gas sensor element, and the oscillation circuit and the heating regulator are linked to a central heating and ventilation control system for the vehicle. Since the further processing of an output signal by the sensor module takes place digitally in the microcomputer of the central heating and ventilation control system, it is possible that the gas sensor element, including the directly linked parts of the evaluation unit, which corresponds to minimal electronic processing, be fitted in a very small housing. The actual processing of the data which comes from the sensor module then takes place in the microcomputer in the heating and ventilation system of the vehicle, which is already present anyway. By using this form of the sensor module it may be ensured that the analog gas sensor signal will then be changed into a digital signal within the sensor module be fed in as a digital signal of the actual evaluation which takes place in the microcomputer of the vehicle's central heating and ventilation system.

Analog signals liable to interference thus do not need to be transported and no complicated analog/digital transformation is necessary within the microcomputer of the central heating and ventilation control unit.

In order to ensure that the reactive sensitivity of metal oxide gas sensor elements in the invented sensor system remains within a positive range with regard to diesel and petrol emission fumes, it is of advantage if the gas sensor element is brought to an operating temperature of less than 250 degrees centigrade, with the operating temperature being held constant by a heating unit.

One disadvantage in the case of previous sensor systems is the fact that the gas sensor elements used in them show major tolerances in their production. A correct electrical impedance match is however only seen of the electrical resistance of the gas sensor element and its external resistance match each other, and the gas sensor current reaches half of the operating current.

Apart from these production tolerances, there are also difficulties with the changing resistance of the gas sensor element which occur as the element gets older, causing problems with reliable and lasting production of impedance match. Furthermore, other sensor systems are negatively influenced by natural moisture which is picked up by working materials, by certain operating conditions and when in contact with certain gases. By connection of d.c. voltage water is removed through hydrolysis. Ion formation takes place and to a high level if ion transport through the crystal mesh of the gas-sensitive layer of the gas sensor element.

The listed above can bring about major alterations in the characteristics of the gas sensor element.

In order to avoid such effects, it is suggested that the ohmic resistance of the gas sensor element be included in an oscillation circuit and should be under medium frequency a.c. voltage.

The frequency of the oscillation circuit will preferably be produced by means of a capacitor.

One particularly advantageous form of the sensor system has a timer unit for the oscillation circuit which is switched with a frequency-fixing capacitor and has s feedback branch, in which the resistance of the gas sensor element and s second resistor are fitted, and which shows a parallel branch to the resistance of the gas sensor element, in which a third resistor is fitted. In this way, the minimum and maximum frequency can be held within limits, even during dramatic changes in the resistance of the gas sensor element. The relation of the gas sensor element resistor, of the in-line switched resistor, and of the one parallel-switched to the former resistor, are so selected that even at extremely low ohmic levels, or extremely high ohmic levels of the gas sensor element or its ohmic resistance, so that the group resistance of the three resistors always remains inside the easily calculated field, which is directly related to the gas sensor signal. Thus it may be ensured that the frequency of the gas sensor signals can never push into a field is outside the recording area of the evaluation electronics of the gas sensor element.

BRIEF DESCRIPTION OF DRAWINGS

The various models of the invention are explained below, referring to illustrations.

The following illustrations show.

BEST MODE FOR CARRYING OUT THE INVENTION

Figure 1:
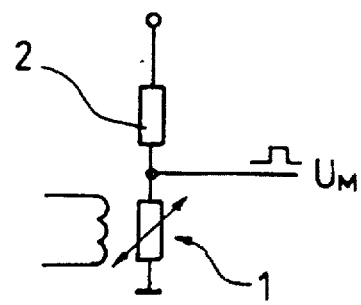
FIG. 1 shows a prior art circuit.
Figure 2:
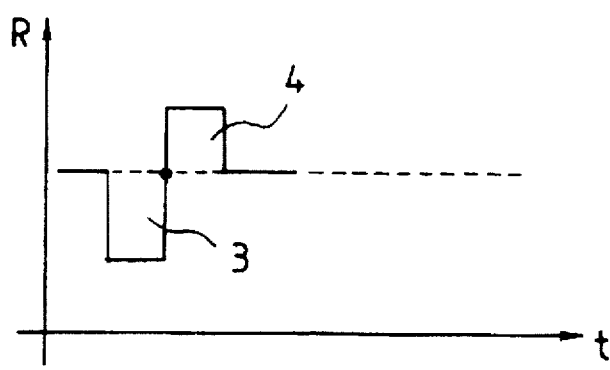
FIG. 2 shows the change in resistance when 1 is coated only with reducing gases.
Figure 3:
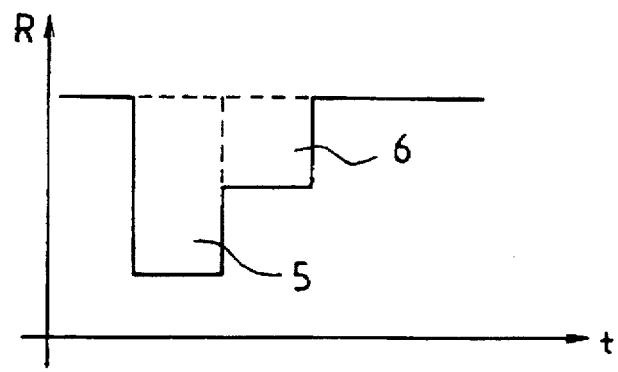
FIG. 3 shows the change in resistance when 1 is in contact with a reducing gas.
Figure 4:
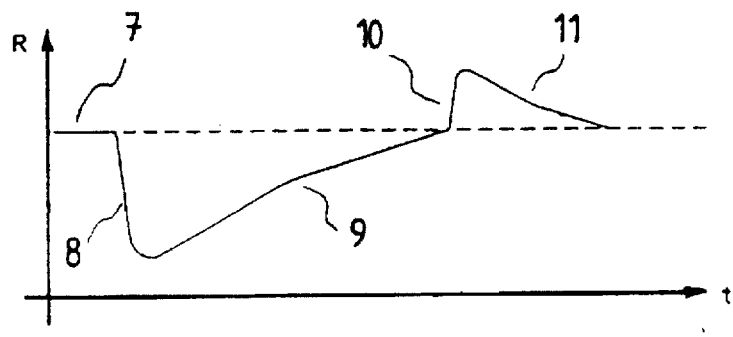
FIG. 4. The process of a gas sensor signal from the invented sensor system.

The conditions which have to be taken into account during the construction of the invented sensor system can be derived from the process of the gas sensor signal illustrated in FIG. 4. The gas sensor signal in FIG. 4 is shown as the resistance value of an ohmic resistor R over time t. At first the gas sensor signal takes on the value 7, which is brought about when the external air is polluted neither with oxidizing gases nor with reducing gases. This value 7 will be left with a large negative rise should oxidable gases appear, as can be seen in the process of the gas sensor signal in phase 8. Here the resistance of the gas sensor element will have a lower ohmic level, whereby the increase correlates to the difference between resistance change and elapsing time. Contact of the gas sensor element with oxidable gases, which are especially prevalent in petrol emission fumes, is followed by a de-adsorption phase 9, during which the gas sensor element is moved through unpolluted outside air and the gas sensor element returns to its original states before contact. This de-adsorption phase lasts until that point in time where the gas sensor signal has once again reached its value 7 for unpolluted air. During the de-adsorption phase 9, the positive increase in the gas sensor signal is much less than the negative increase of the gas sensor signal during the adsorption phase named phase 8. The relation of the resistance change per unit of time is noticeably smaller during the de-adsorption phase 9 than during the adsorption phase 8.

Once the gas sensor signal has once again taken on its value 7 for unpolluted external air, the gas sensor element runs through an area in which the external air is loaded with reducible gases. Because of the contact by the gas sensor element with these reducible gases, an adsorption phase 10 takes place, during which the resistance value of the gas sensor element is greatly increased due to the oxidizing effect of the reducible gases. The positive increase of the gas sensor signal during adsorption phase 10 are approximately equivalent to the negative increase of the gas sensor element during adsorption phase 8. Once the area containing the air loaded with reducible gases has been passed through, de-adsorption phase 11 begins, during which the gas-sensitive layer of the gas sensor element de-adsorbs. The de-adsorption phase takes place in the unpolluted outer air, until the gas sensor signal has once again adopted the original value 7. The negative increase which arises from the change in the resistance value per unit of time amounts during de-adsorption phase 11 to the numeric equivalent of the positive increase during the preceding de-adsorption phase 9. It may be observed from FIG. 4 that the change in resistance per unit of time during the de-adsorption phases 9 and 11 is noticeably lower than during the adsorption phases 8 and 10.

The increase of the gas sensor signal is negative during the adsorption phase of a gas sensor element in contact with oxidable gases and during the de-adsorption 11 of a gas sensor element in contact with reducible gases; the increase is positive during de-adsorption phase 9 of a gas sensor element in contact with oxidable gases and during adsorption phase 10 of a gas sensor element in contact with reducible gases.

Characteristic for the process of the gas sensor signal is the difference between the numerically variant increase values during adsorption phases 8 and 10, and the de-adsorption phases 9 and 11. This characteristic of the gas sensor signal is used in the case of this invention in order to set up objective switch criteria.

When a fall in the gas sensor signal together with a change in the gas sensor signal per unit of time that exceeds a preset limit is noted, the gas sensor element has been in contact with oxidable gas. When a rise in the gas sensor signal together with a change in the gas sensor signal per unit of time that exceeds a preset limit is noted, then the gas sensor element has been in contact with reducible gas. The above rules are valid for every change in the gas sensor signal, independent of the direction of change of the gas sensor signal, and also independent of the starting level of the gas sensor signal at the point in time at which an appropriate increase or fall is measured.

Figure 5:
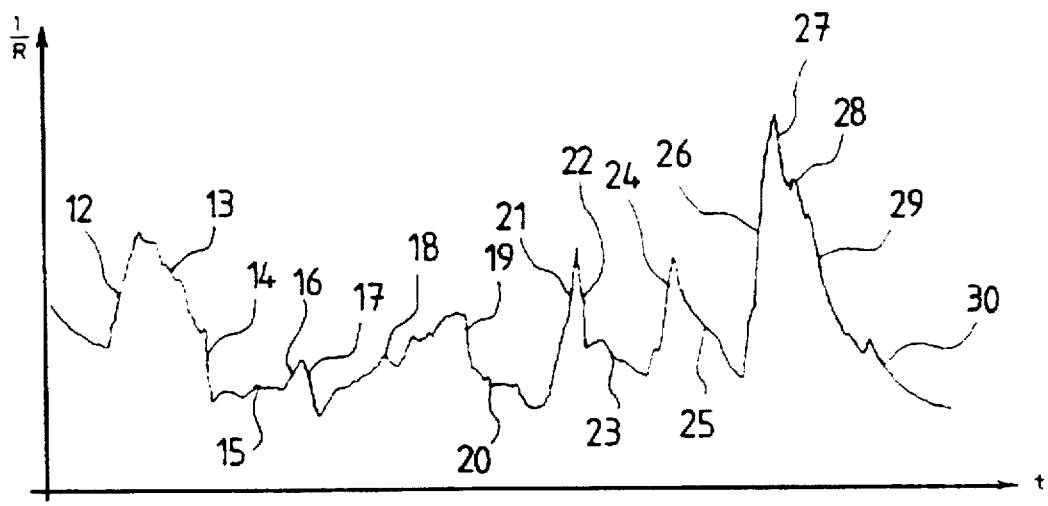
FIG. 5. The process of the gas sensor signal during road surveying work in traffic.

Normal road traffic movements do not usually cause situations under which the gas sensor element can return to its original condition following every contact with reducible or oxidable gases and the adsorption phase which results, followed by a de-adsorption phase, which occurs with contact to unpolluted air. Rather more, contact with reducible or oxidable gases normally takes place during adsorption and de-adsorption phases which have already started due to other contacts. A typical process for a gas sensor signal is illustrated in FIG. 5. The reciprocal value of the resistance value for the gas sensor element is shown over time.

At first the gas sensor element is in contact with oxidable gases which originate from petrol exhaust emissions, from which the adsorption phase 12 with its large increase is derived. The end of adsorption phase 12, which occurs before the gas-sensitive layer of the gas sensor element is saturated with oxidable gases, will be followed by de-adsorption phase 13. During de-adsorption phase 13 the gas-sensitive layer of the gas sensor element de-adsorbs, whereby the de-adsorption speed is noticeably slower than the adsorption speed during adsorption phase 12. From this it may be noted that the negative increase in the gas sensor signal during de-adsorption phase 13 is measurably lower than the positive increase in the gas sensor signal during adsorption phase 12. During de-adsorption phase 13 the gas sensor element is in contact with reducible gases, for example NO and NOx, as contained in diesel emission fumes. Following this is an adsorption phase 14 with a large increase, whereby the increase of adsorption phase 14 is numerically equivalent to the preceding adsorption phase 12. With regard to the process of the gas sensor signal, the adsorption phase 14 differentiates itself from de-adsorption phase 13 insofar as that increase of adsorption phase 14 is noticeably greater than the increase during de-adsorption phase 13.

The end of adsorption phase 14, which occurs before the gas-sensitive layer of the gas sensor element is saturated with oxidizable gases, will be followed by de-adsorption phase 15, a light coating of the gas sensor element with oxidable gases and resulting small adsorption phase 16, immediately followed by a short term coating of the gas sensor element with large quantities of reducible gases which could originate from the exhaust system of a lorry, and the resulting adsorption phase 17, a de-adsorption phase 18, a renewed coating with reducible gases which leads to adsorption phase 19, a de-adsorption phase 20, a coating with oxidable gases, which leads to adsorption phase 21, a coating with reducible gases, which leads to adsorption phase 22, a de-adsorption phase 23, a coating of the gas sensor element with oxidable gases, which leads to adsorption phase 24, a de-adsorption phase 25, a renewed coating of the gas sensor element with oxidable gases, which leads to adsorption phase 26, a coating of the gas sensor element with reducible gases, which leads to adsorption phase 27, a short de-adsorption phase 28, a renewed coating of the gas sensor element with reducing gases, which leads to adsorption phase 29, and a de-adsorption phase 30.

From the representation of the gas sensor signal in FIG. 5 it can clearly be seen that the increase in the adsorption phases is numerically clearly greater than the increase in the de-adsorption phases. The principle of the invention is based on setting a lower limit value for the increase of the gas sensor signal, with the result that a switching of the vehicle ventilation system from air input to recirculation mode will always occur when the increase in the gas sensor signal exceeds this limit value.

With the switching behavior of the ventilation system stated above, the input into the vehicle of the suddenly polluted external air can be avoided. This switching behavior is however not suitable for preventing the air quality inside the vehicle from being affected by a situation where a gradual increase in pollutants in the air surrounding a vehicle, which may occur in tunnels or other heavy traffic situations, is taking place.

Figure 6:
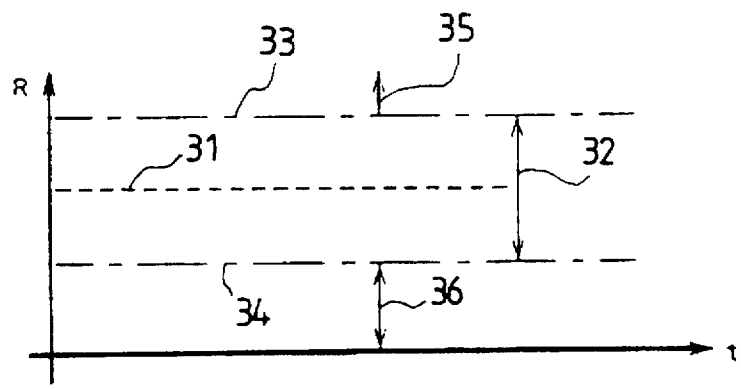
FIG. 6. A band which serves as switch criterion for the invented sensor system.

In order to also prevent such prevailing quality deteriorations in the air surrounding the vehicle which also lower the quality of the atmosphere within the vehicle, a value with a mean of 31 is calculated from the gas sensor signal by integration or similar means, valid for a set period of time, as shown in FIG. 6. A band 32 is constructed around this mean value 31, which can take place through subtraction and addition of an absolute or by supplement or deduction based proportionally on the value 31. This band 32 allotted to the mean value 31 is limited by the upper value 32 and by the lower limit 34, whereby the upper value 33 and the lower value 34 mark the positive/negative proportional or absolutely permitted deviation of the gas sensor signal from the mean value 31.

A switch signal to switch the vehicle ventilation system from air input mode to recirculation mode will then be generated whenever the current gas sensor signal lies outside the field of band 32 and thus inside the fields 35 or 36.

Figure 7:
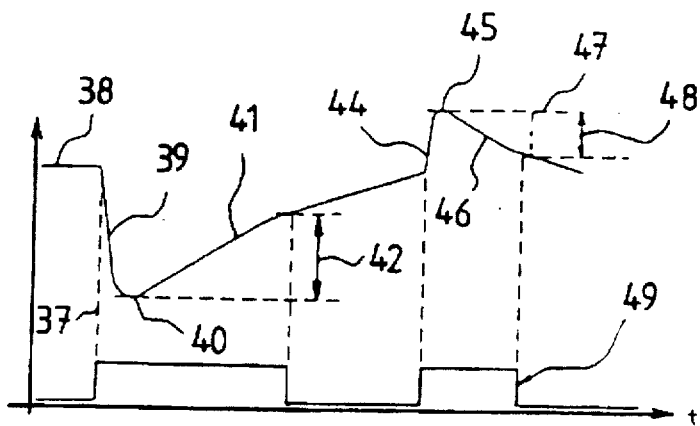
FIG. 7. A further method of creating switch criteria for the invented sensor system.

The signal to switch the vehicle ventilation system from air input mode to recirculation mode must be generated at a moment in time from when the quality of the air surrounding the vehicle is of an acceptable standard. In order to achieve such switching behavior, recirculation mode will be activated when,—as can be seen in FIG. 7, at time point 37 a fall starts in the gas sensor signal, whereby the negative increase of this fall in the gas sensor signal is greater than the reciprocal value mentioned above. Before time point 37 the gas sensor signal runs at its normal value 38 which it has in unpolluted atmospheric conditions. During adsorption phase 39, following time point 37, the gas sensor signal falls to inversion point 40, at which the de-adsorption phase 41 begins, following adsorption phase 39. At inversion point 40 the sign for the increase in the gas sensor signal changes from a negative sign during adsorption phase 39 to a positive sign during de-adsorption phase 41. Through this sign change for the increase of the gas sensor signal inversion point 40 is recognized and stored in the evaluation unit. Furthermore, the gas sensor signal at the time of inversion of the sign of the gas sensor signal will be linked to this inverse point 40. A freely determinable difference value 42 is stored in the evaluation unit. If the gas sensor signal level during de-adsorption phase 41 leading from inversion point 40 increases by the difference value 42, there follows a switching of the vehicle ventilation system from recirculation mode to air input mode. Before the switching operation is initiated, the evaluation unit checks to see whether the gas sensor signal is actually within the band 32 illustrated in FIG. 6.

At time point 37 the gas-sensitive layer of the gas sensor element is coated with an oxidizable gas. After the completion of de-adsorption phase 41, the gas-sensitive layer of the gas sensor element is again coated with a reducible gas. At the beginning of this contact at time point 43, the increase of the gas sensor signal changes from the comparatively low value during the de-adsorption phase 41 to the relatively high value during the adsorption phase 44, which takes place following time point 43. The increase in the gas sensor signal during adsorption phase 44 exceeds the preset limit value, so that a switching of the vehicle ventilation system from air input to recirculation mode takes place at time point 43. Adsorption phase 44 leads to de-adsorption 46 after the coating of the gas-sensitive layer in the gas sensor element by reducible gases at inversion point 45 has ended. The sign for the increase of the gas sensor signal changes at inversion point 45, between adsorption phase 44 and de-adsorption phase 46. Through this change of sign, inversion point 45 will be recognized and stored in the evaluation unit. In addition, gas sensor signal level 47 is stored in inversion point 45 in the evaluation unit. Furthermore, a difference value 48 is stored in the evaluation unit and may be freely allotted. The difference value 48 for de-adsorption phase 46, following a coating with reducible gases, can be the equivalent of the difference value 42 for de-adsorption phase 41 following coating with oxidable gases, but may nevertheless be different since diesel and petrol exhaust emissions are not sensed in the same way.

If the gas sensor signal, leading from inversion point 45, during de-adsorption phase 46 falls below gas sensor signal level 47 at inversion point 45 by the difference value 48, then the vehicle ventilation switches from recirculation mode to air input operation.

Graph 49 shows the operational state of the ventilation system. From graph 49 it may be seen that the ventilation system worked in recirculation mode until switching into air input mode, from tim point 37 following an increase by difference value 42 in the de-adsorption phase 41 leading from inversion point 40 and between time point 43 and the fall by difference value 48 in de-adsorption phase 46 which follows inversion point 45.

Figure 8:
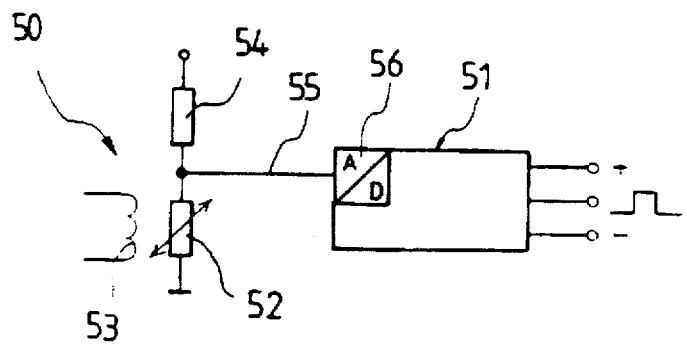
FIG. 8. A typical evaluation unit.

The basic construction of the sensor system invention is illustrated in FIG. 8.

A sensor part 50 and an evaluation unit 51 belong to the sensor system.

Sensor part 50 has a gas sensor element 52, which has an changeable ohmic resistance and is held by means of a heating unit 53 at an operating temperature of less than 250 degrees centigrade. Furthermore, sensor part 50 has an external resistor 54. A gas sensor signal measured between gas sensor element 52 and external resistor 54 is fed into the evaluation unit through a connection cable 55. This central evaluation unit 51 serves not only to evaluate the gas sensor signal data it receives through the connection cable 55, but also to control the vehicle ventilation system which is not shown in FIG. 8.

The evaluation unit 51 is fitted with an integrated analog/digital transformer 56, which changes the analog gas sensor signal fed into the evaluation unit 51 into a digital signal. Additionally, a programme run is digitally stored in the evaluation unit 51, by means of which a switch signal may be generated using the switch criteria explained in FIGS. 4–7, switching the vehicle ventilation system from air input to recirculation mode and vice-versa.

Figure 9:
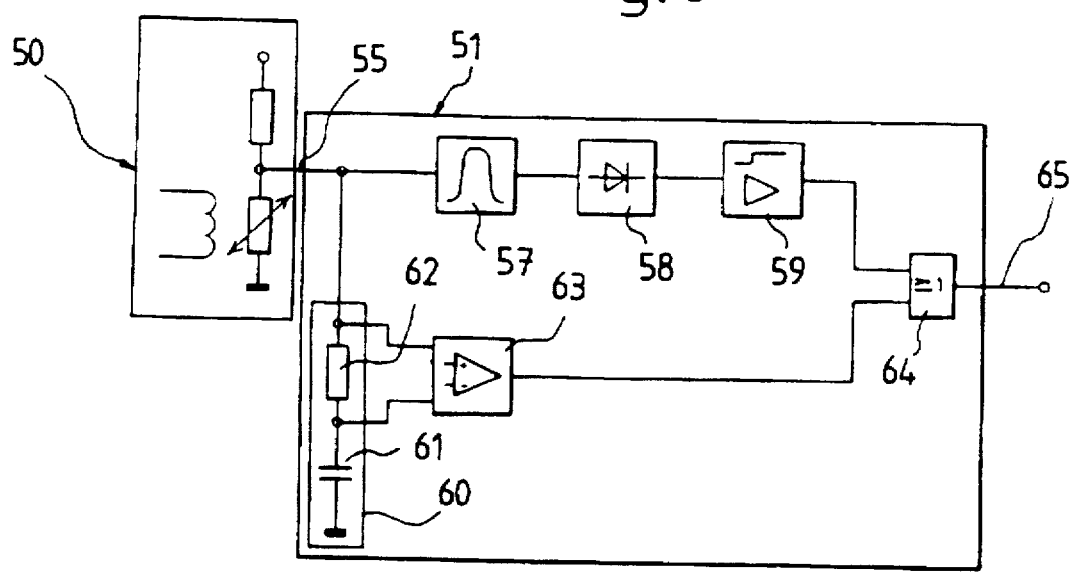
FIG. 9. A further model of the evaluation unit for the invented sensor system.

In the model of the sensor system which is illustrated in FIG. 9, the sensor part 50 is the same as sensor part 50 described in FIG. 8 above. The gas sensor signal travels from sensor part 50 through the connection cable 55 into evaluation unit 51.

In evaluation unit 51 the gas sensor signal travels through a band pass 57. Band pass 57 is so arranged that only those amplitude spectrums can pass which are typical for a process of the gas sensor signal, when the gas sensor signal changes in line with an adsorption phase occurring in gas sensor element 52. This means that band pass 57 can only allow those amplitude spectrums to pass, whose gas sensor signal increases are signalled as exceeding the preset threshold. In this respect it should once again be said that gas sensor element 52 is so set up (in a way described below) that the increase during its contact with oxidable gases and the resulting adsorption phase is the same as the increase during coating with reducible gases and the resulting adsorption phase.

The start signal of band pass 57 is rectified in demodulator 58. The rectified start signal from demodulator 58 triggers a comparator with a freely selected shifter shaft if the level is correct. In this manner, a switch signal for the ventilation system will always be generated when the vehicle fitted with the invented sensor system drives through areas where the outside atmosphere is polluted, whereby the sensor system's switching behavior is independent of whether or not the level of impurities in the air derive from diesel or petrol emissions.

This switch signal remains at the output of comparator 59 as long as the gas sensor element 52 of sensor part 50 is in the adsorption phase. Saturation of gas sensor element 52 almost never occurs in practise, since the vast majority of the impurities found in the outside atmosphere are of relatively short term nature, due to the fact that the vehicle will move through the atmosphere during the course of normal operation. Adsorption phases last a few minutes at the most, so that gas sensor element 52 will normally not be held in a saturated state.

There are however traffic situations in which a saturation of gas sensor element 52 cannot always be avoided. The placing of gas sensor element 52 in the saturation zone may for example occur when the vehicle remains for a longer period of time in an area where the outside atmosphere is heavily polluted. In such a case, the increase in the gas sensor signal will move towards zero, although the pollution of the outside atmosphere remains unchanged or may even deteriorate. Without further measures the vehicle ventilation system would, in such a traffic situation, switch recirculation mode to air input mode, since the gas sensor signal in such a traffic situation would now show the frequency bands that could travel through band pass 57.

Since such situations may occur for example in traffic tunnels and heavy traffic jams, the actual level of the gas sensor signal will be measured and processed in the evaluation unit. In this way, the gas sensor signal fed into the evaluation unit 51 through the connection cable 55 is fed into an resistance capacitor circuit, by means of which it may be integrated with a high time constant. Accordingly, a mean value for the gas sensor signal forms in a capacitor 61 of the resistance capacitor circuit. Whenever the gas sensor signal takes on a higher value than the mean value which is in the capacitor 61 of the resistance capacitor circuit 60, current builds up in load resistor 62 in the resistance capacitor circuit, which is the equivalent of the difference between current gas sensor signal and the mean value of the gas sensor signal which is in capacitor 61 of the resistance capacitor circuit. This current is fed into a comparator 63, by which means a switch signal will always be generated, if the current gas sensor signal is greater than the quasi 'stored' mean value in capacitor 61 of the resistance capacitor circuit 60.

By correct selection of the time constant of the resistance capacitor circuit 60 in the traffic situations described above, where the atmosphere surrounding the vehicle is subject to lasting high pollution levels and thus the gas sensor element 52 can be saturated, it can be ensured that the vehicle ventilation system can remain in recirculation.

Even when the vehicle is surrounded by very high levels of pollution for a prolonged period of time, it is still desirable that the vehicle ventilation system should once again switch from recirculation mode to air input mode after a predetermined period of time; otherwise the oxygen consumption by the vehicle passengers, the moisture and other physiological factors deriving from those in the vehicle would rapidly lead to a fall in the air quality inside the vehicle. In order to avoid such a situation arising, the time point is stored in the evaluation system, at which the vehicle ventilation system switches from air input to recirculation mode. At the end of a preset period of time, the length of which is dependent on the volume of the inside of the vehicle, as well as the measured number of persons travelling in the vehicle, the vehicle ventilation system will be forcibly switched from recirculation mode to air input mode, as long as, within the time space in question, no switch from recirculation mode to air input has taken place due to an alteration in the level of the pollution in the atmosphere surrounding the vehicle. The output signal from comparator 59 and the output signal from comparator 63 of evaluation unit 51 will be linked together in linking unit 64. The output signal from linking unit 64 will be fed into the controller of the ventilation system through output cable 65 of linking unit 64 or evaluation unit 51 as a switching signal.

In a preferable model of the invented sensor system the circuit functions explained above using analog function groups will be computer constructed. This then allows a microprocessor controlled process allowing, according to the desired switch behavior explained above, switch signals for the switching of the vehicle ventilation system from air input to recirculation mode, or vice-versa, to be received.

Gas sensor element 52 is preferably constructed as a mixed oxide sensor element, whereby its gas-sensitive layer contains approximately 39% tin dioxide, approximately 10% ferric oxide, approximately 38% tungsten trioxide, approximately 10% aluminium oxide, approximately 2% palladium and approximately 1% platinum, whereby the palladium and the platinum function as reaction accelerators.

In a preferred model version of the invented sensor system the gas sensor element will be run at an operating temperature that lies under 200 degrees centigrade. At such an operating temperature for gas sensor element 52, its reactive sensitivity towards oxidable gas is greatly reduced. The reactive sensitivity of gas sensor element 52 towards reducible gases is however comparable with the reactive sensitivity at other temperatures. In this way it may be ensured that, in view of their disturbance potential for the vehicle passengers, comparable coating of the gas sensor element 52 with reducible and oxidable gases will produce approximately the same, even if directionally different, alterations of the gas sensor signal. In view of this evenhanded sensitivity of the gas sensor element 52 towards oxidizable and reducible gases, it is possible to use the alteration of the gas sensor signal per unit of time, that is the figure for the increase in the gas sensor signal, as a switching parameter for the vehicle ventilation system.

In a further preferred model of the invented sensor system the sensor part 50, together with evaluation unit 51, are fitted in one common housing.

Figure 10:
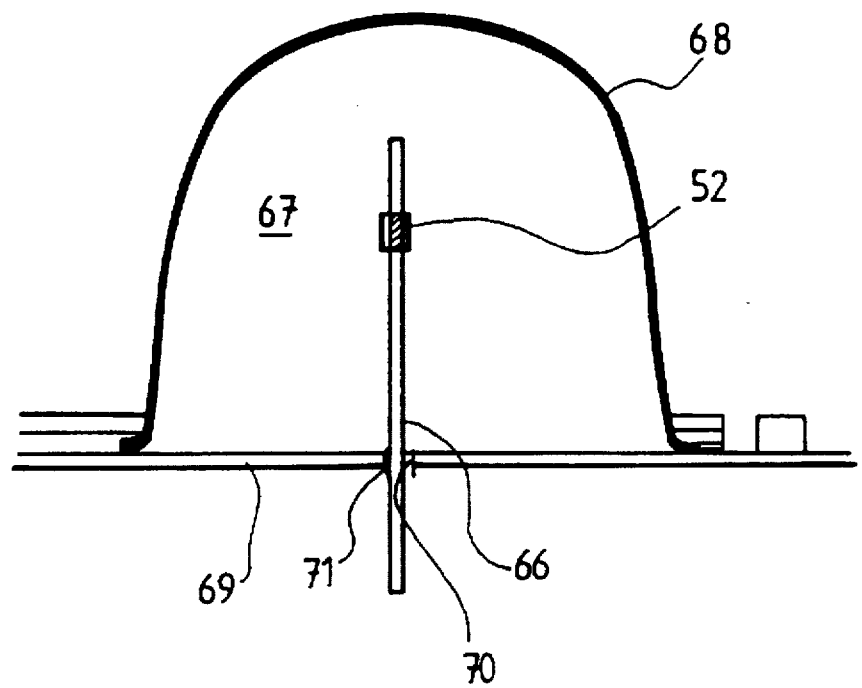
FIG. 10. A model of a gas sensor element fitted in a chamber.

In the model illustrated in FIG. 10 the gas sensor element is mounted on a circuit board 66 and fitted inside chamber 67. Chamber 67 is formed by a wall or screen 68 and by horizontal plate 69. Horizontal plate 69 has an opening 70 in its cross-section, approximately equivalent to that of circuit board 66, through which circuit board 66 stretches into chamber 67. Between the inside of opening 70 and that part of circuit board 66 which is inside the opening, sealant material 71 is intended. Gas sensor element 52 is directly mounted here on circuit board 66, whereby circuit board 66 provides the connection to the evaluation 51, which is not illustrated in FIG. 10. In this model, the evaluation unit 51 is fitted in a separate housing. Chamber 67 and the housing for evaluation unit 51, not illustrated in FIG. 10, are hermetically sealed from each other by means of the horizontal plate 69 and the sealant material 71. Such a hermetical division is required, in order to minimize the decay time for example of gas sensor element 52 and to exclude any distortion factors which may for example derive from the electronic components in evaluation unit 51 warming in the emissions, or warming plastic parts.

The wall/screen 68, which surrounds gas sensor element housing chamber 67 is constructed on a gas-permeable basis. In this way, rapid and unhindered gas exchange between chamber 67 and the air surrounding wall/screen 68 can take place.

One constituent part of the wall 68 is a gas-permeable film 72. Teflon has proven itself to be an especially suitable material for this film.

Figure 11:
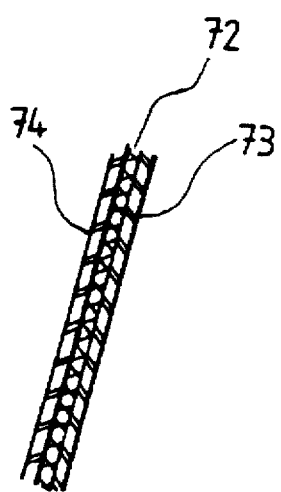
FIG. 11. A model of the gas sensor element chamber wall as in FIG. 10.

The film 72, is as can especially be seen in FIG. 11, covered and supported on both sides by stable wall sections 73 and 74. It is so mounted between wall sections 73 and 74 that vibration of film 72 may be excluded in any case.

Wall sections 73 and 74 can be in the form of drawn form parts of woven wire or as drawn perforated metal or plastic.

The wall/screen 68 can cup-shaped or hemispherical in form, whereby the stability of the shape may achieved by pressing a teflon film 72 with glass-fibre strengthened plastic to the required wall or screen 68.

In another model the wall or screen 68 used to protect against mechanical wear can be formed of a gas-permeable sinter body or of a gas-permeable plastic body.

Figure 12:
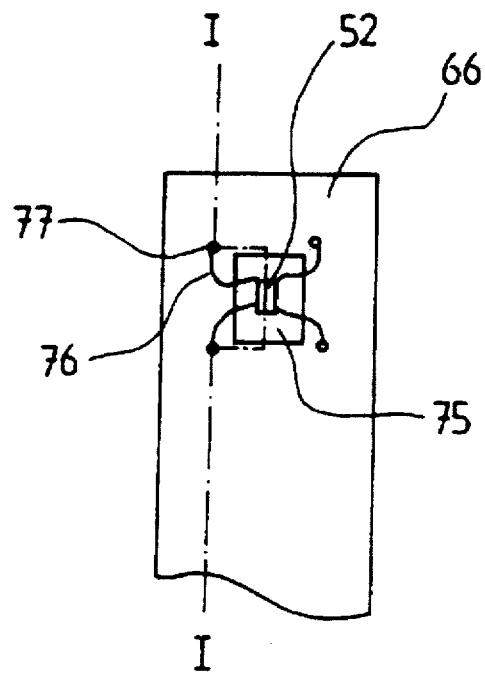
FIG. 12. A top view of the auxiliary circuit board with gas sensor element shown in FIG. 10.
Figure 13:
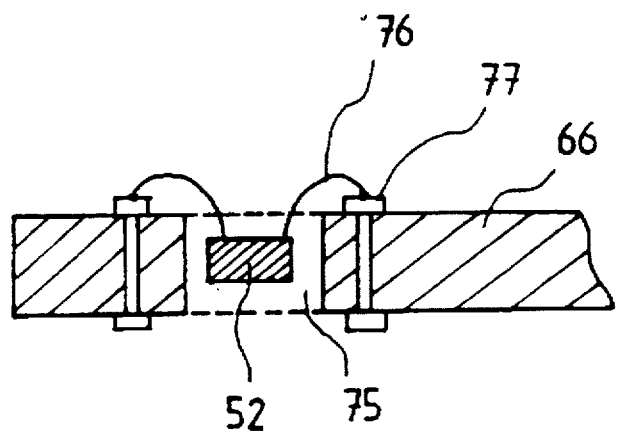
FIG. 13. A side projection of the auxiliary circuit board scale 1:1 in FIG. 12.

One possibility for mounting gas sensor element 52 on circuit board 66 is shown in FIGS. 12 and 13, whereby FIG. 13 represents excerpt I—I in FIG. 12.

A rectangular cut-out 75 exists in circuit board 66. Cut-out 75 is positioned in the free end section of that part of circuit board 66 which extends into chamber 67.

Gas sensor element 52 is positioned in the middle part of cut-out 75 in circuit board 66. Gas sensor element 52 is linked to connection cables 76, made of platinum or any other suitable precious metal and which are connected to connection pins 77, fitted in the area surrounding cut-out 75 in circuit board 66. The mounting of gas sensor element 52 thus takes place using connection cables 76 and the circuit board-side connection pins 76. The connection pins 76 could for example be made of nickel.

The fitting of gas sensor element 52 in cut-out 75 of circuit board 66 is so selected that the gas sensor element 52 is positioned in the exact center of the cut-out 75 of circuit board 66, as measured in every dimension.

Figure 14:
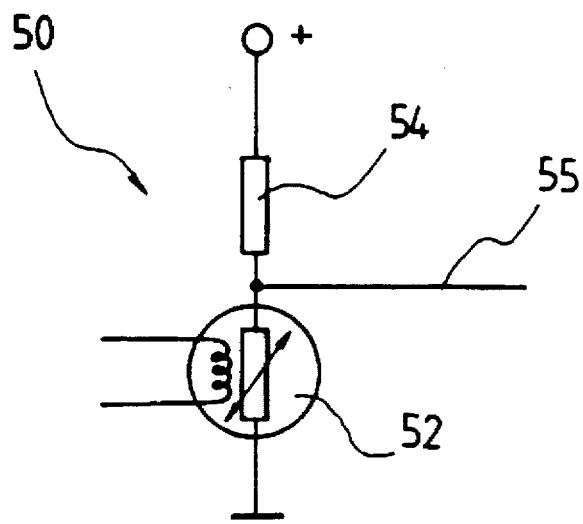
FIG. 14. The principles of a gas sensor element.
Figure 15:
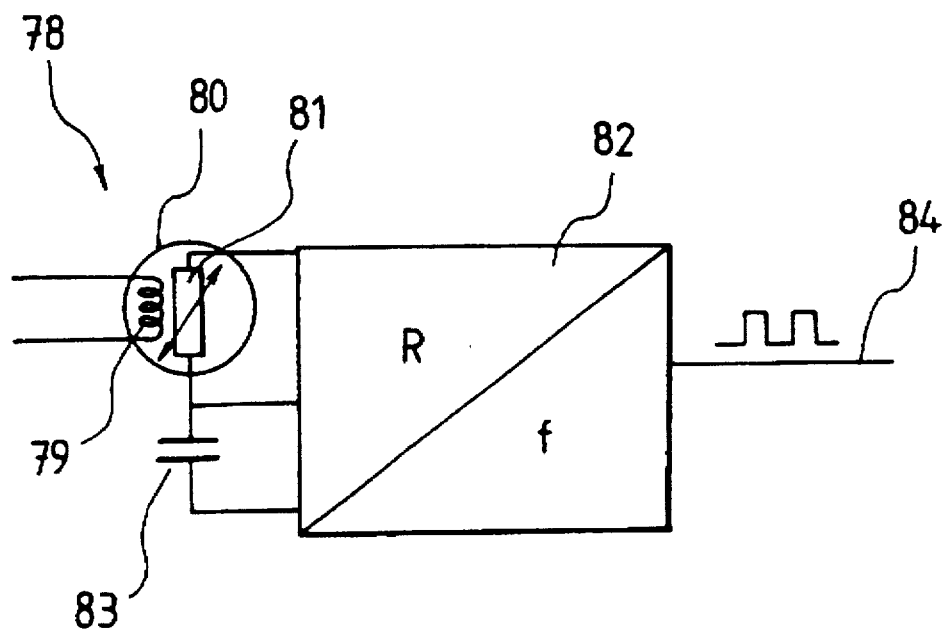
FIG. 15. The principles of one of the primary models of the gas sensor element from the invented sensor system.

Instead of the sensor part 50 illustrated alone in FIG. 14, which shows the gas sensor element 52 with ohmic resistance changed according to gas contact, heating unit 53 and outside resistor, whereby the actual gas sensor signal is transmitted through connection wire 55 to evaluation unit 51, which is not illustrated, the invented sensor system can make use of sensor part 78, which is illustrated in FIG. 15 and described below. In the case of the sensor part 78 illustrated in FIG. 15, a gas sensor element 80 which can be heated using a heater unit 79 is planned, the ohmic resistance 81 of which is combined with oscillation circuit 82, which has a further frequency fixing component of a capacitor 83. The oscillation circuit 82 produces an output signal, which is fed through cable 84 to a further evaluation unit.

Figure 16:
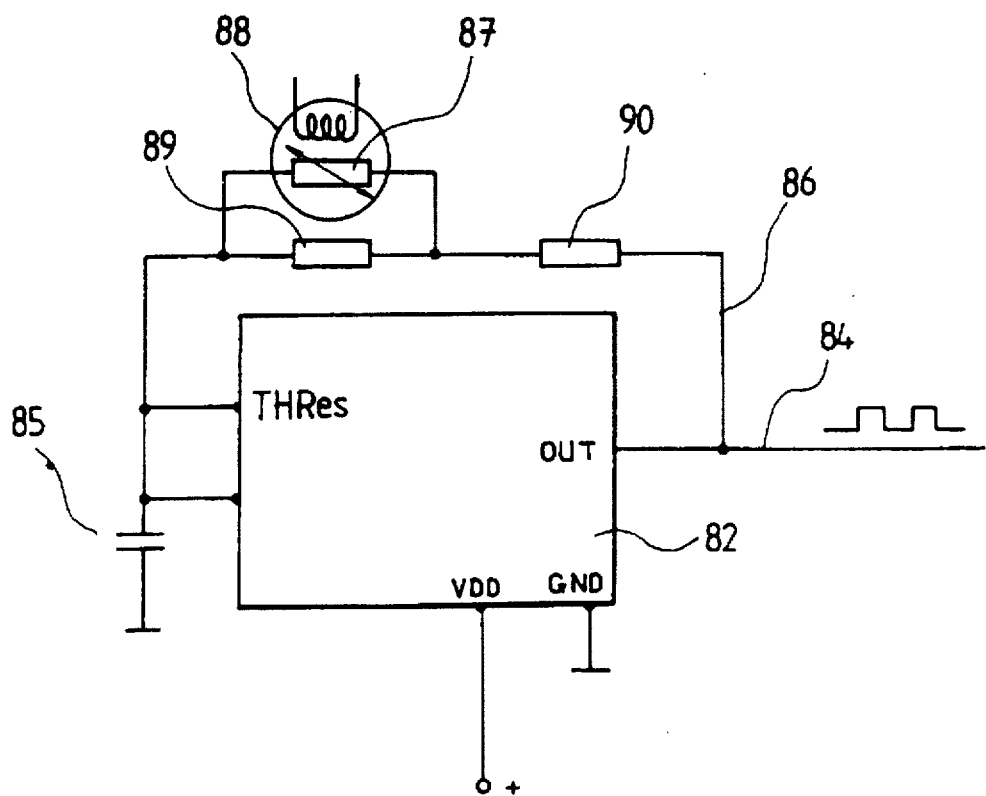
FIG. 16. The principles of a further model of the gas sensor element from the invented sensor system.

In one practically applicable model, as illustrated in FIG. 16, circuit 82 is planned as an electronic standard component in the form of, for example, a timer 555. This timer component is switched with frequency fixing capacitor 85.

Timer component 82 has a feed-back branch 86. Feedback branch 86 has an ohmic resistance 87 of a gas sensor element 88, adjustable according to gas coating, with a parallel-switched resistor 89. A third resistor 90 is planned for feed-back branch 86, in series to the sequence of the parallel switched resistor 87 and 89.

Through the parallel switching of the second resistor 89 to resistor 87 of gas sensor element 88 and the serial switching of the third resistor to the sequence of the parallel switched resistors 87 and 89, the minimum and maximum frequency will be limited, even in the case of a dramatic change in resistor 87 of gas sensor element 88 following sudden and strong gas contact. The relations between the three resistors 87, 89 and 90 are so selected that both in case of extremely low ohmic level and in the case of extremely high ohmic level in resistor 87 of the gas sensor element 88, the group resistance of resistors 87, 89 and 90 always remain inside an easily calculated range, related directly to the frequency of the initial signal. In this way it may be ensured that the frequency of the initial signal or of the gas sensor signal will never move into a field which is outside the operating range of the switched evaluation unit.

Figure 17:
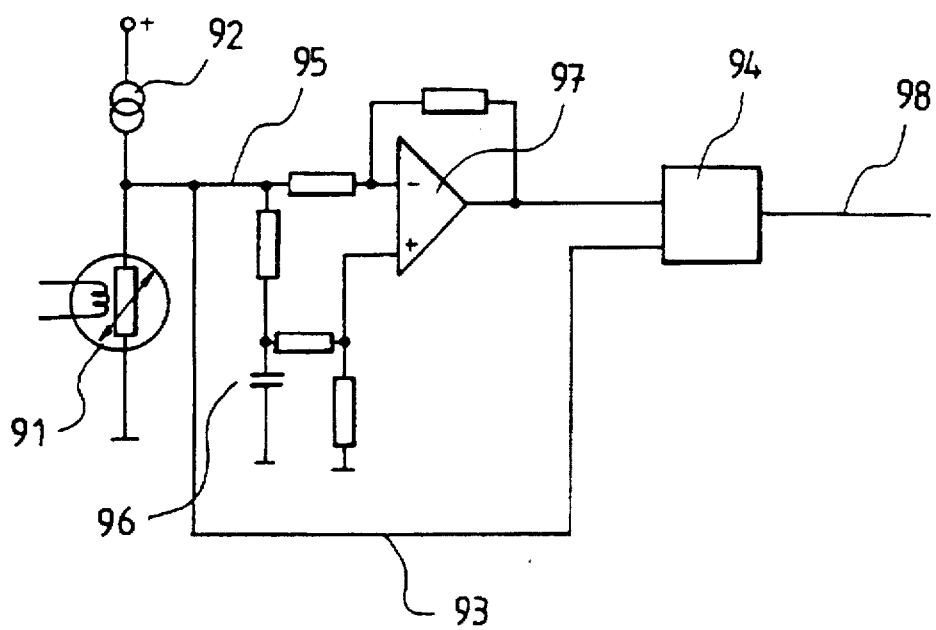
FIG. 17. The principles of a circuit for the separation of basic pollution from dynamically occurring peak pollution levels.

FIG. 17 shows a switching system by means of which basic pollution can be differentiated from peak levels of pollution. Basic pollution of the atmosphere outside the vehicle, such as that which may be experienced in a rural area, is very different to that degree of impulsive, dynamic peak pollution levels which might well be faced in an inner-city area, such as would be experienced behind a diesel-powered lorry or at a particularly busy road traffic junction. With this switching system, it is assumed that, based on past experience, basic pollution levels change extremely slowly, whereas on the other hand the pollution levels produced by a vehicle driving in front may change extremely quickly.

A gas sensor element 91 illustrated in FIG. 17 is fed by a constant source of current 92. The gas sensor current measured between the constant current source 92 and gas sensor element 91 is fed by means of a cable 93 to a divider 94.

A cable 95 branches from the cable 93, by means of which the gas sensor signal will be fed into an integrator 96, by means of which a comparative signal will be generated for an operation amplifier 97. The gas sensor signal is fed directly into the other input of the operation amplifier 97. The output signal from operation amplifier 97 is also fed to divider 94.

In an output cable 98 of divider 94, an output signal is made available, by means of the fact that changing base pollution means slowly-changing signal parts of the gas sensor signal depending on the time constant of the time unit or integrator 96 are separated from the gas sensor signal. The output signal in the output cable 98 of divider 94 only contains the part signal from the gas sensor signal which shows the dynamic peak pollution levels.

In FIGS. 18 to 21, further circuit models are illustrated, by means of which the possibility of so processing the gas sensor signal exists that the reactive sensitivity of the invented sensor system will be controlled dependent on those part signals from the gas sensor signal which derive from the previously-mentioned dynamic peak pollution levels.

Figure 18:
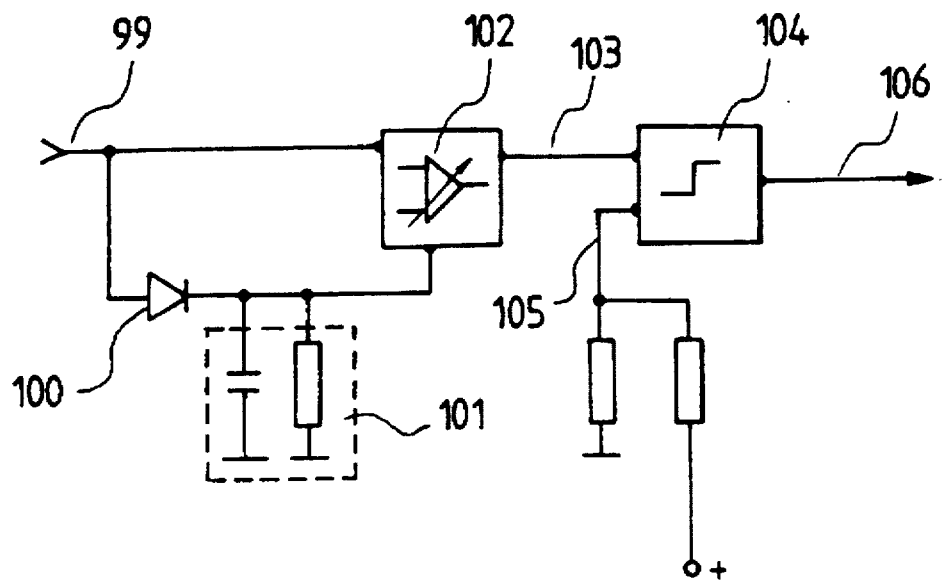
FIG. 18. to FIG. 21. Principles of signal processing circuits for the regulation of reactive sensitivity of the invented sensor system.

In the example illustrated in FIG. 18, the sensor signal is fed through a cable 99 to a diode 100, through which the gas sensor signal 99 charges a resistance capacitor circuit; in this way a current will be created, and fed to a adjustable amplifier 102.

The level of the output signal in the output cable 103 of the adjustable amplifier 102 is therefore dependent of the charge condition of the resistance capacitor circuit 101, which is logically dependent on the dynamics and frequency of the gas sensor signal.

A switch amplifier 104, fitted after the adjustable amplifier, for which output cable 103 of the adjustable amplifier functions as input cable, has a fixed set trigger level which is fed into the switch amplifier 104 through input cable 105. The switch amplifier 104 then produces a switch signal in its output cable 106 whenever the adjusted gas sensor signal level exceeds the limit preset by means of the trigger level.

Figure 19:
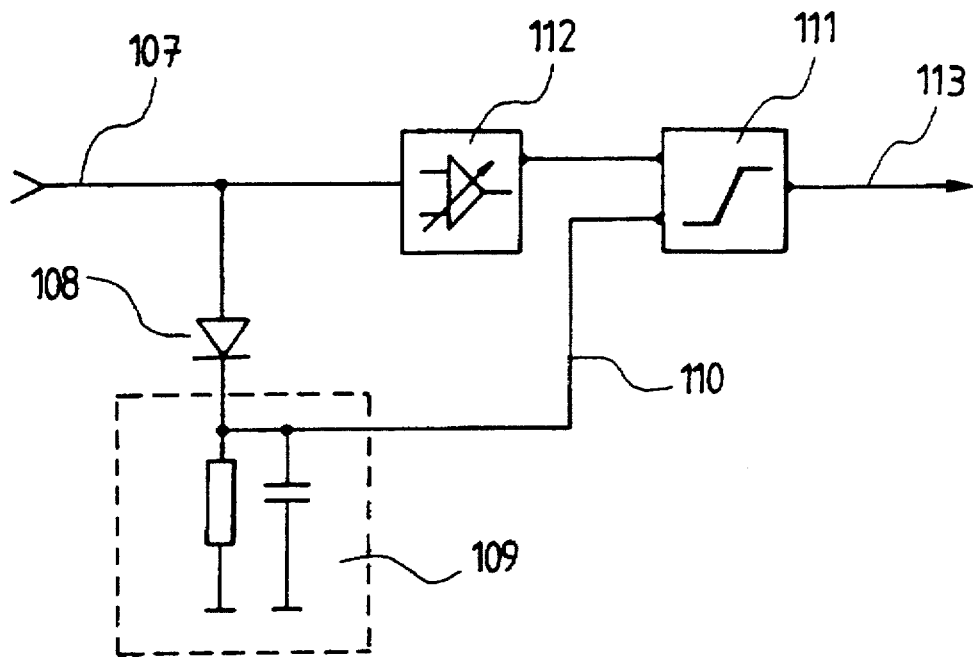

As in the case of the model illustrated in FIG. 18, the so-called dynamic signal works for the model illustrated in FIG. 19. The dynamic signal contains merely those part signals which derive from dynamic coating of the gas sensor element, due to impulsive peak pollution levels. These part signals are transmitted through a cable 107 to a diode 108, through which a resistance capacitor circuit 109 will be charged. The current produced by means of resistance capacitor circuit 109 is fed into a circuit amplifier 111 through a connection link cable 110, by means of which amplifier 111 has a signal-dependent and thus variable trigger current.

Furthermore, the dynamic gas sensor signal is fed into switch amplifier 111 through amplifier 112, whereby it triggers the switch amplifier 111, according to the switch threshold, that is to say according to the variable trigger current produced by the resistance capacitor circuit. A switch signal will then be generated in an output cable 113 of switch amplifier 111.

Figure 20:
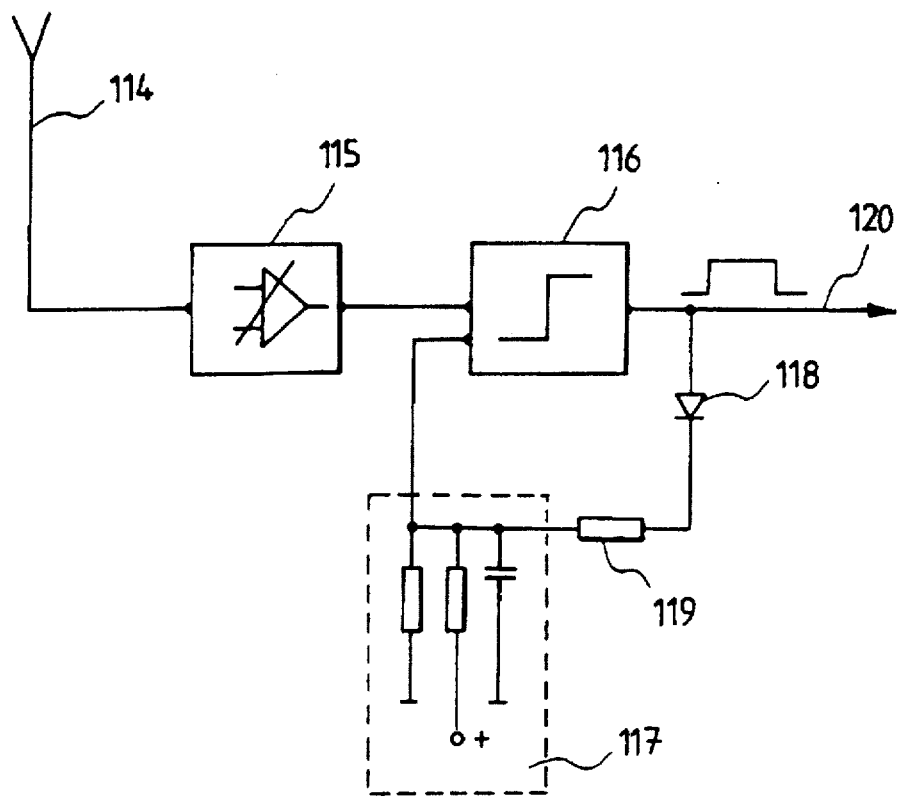

FIG. 20 shows an illustration of a further model, in which the dynamic gas sensor signal, explained above and mentioned on several occasions, travels along cable 114 through an amplifier 115 before being fed into switch amplifier 116.

The switch current derives from the current of a current divider with switched capacitor circuit 117, whereby the current of the output signal in an output cable 120 of switch amplifier 116 through a diode 118 and a charge resistor 119 influences the capacitor circuit 117, with the tendency that, as long as there is frequently output or switch signal in the output cable 120 of switch amplifier 116, the trigger threshold of switch amplifier 116 is so altered that the switch system reacts less sensitively to changes in the dynamic gas sensor signals travelling through cable 114.

Figure 21:
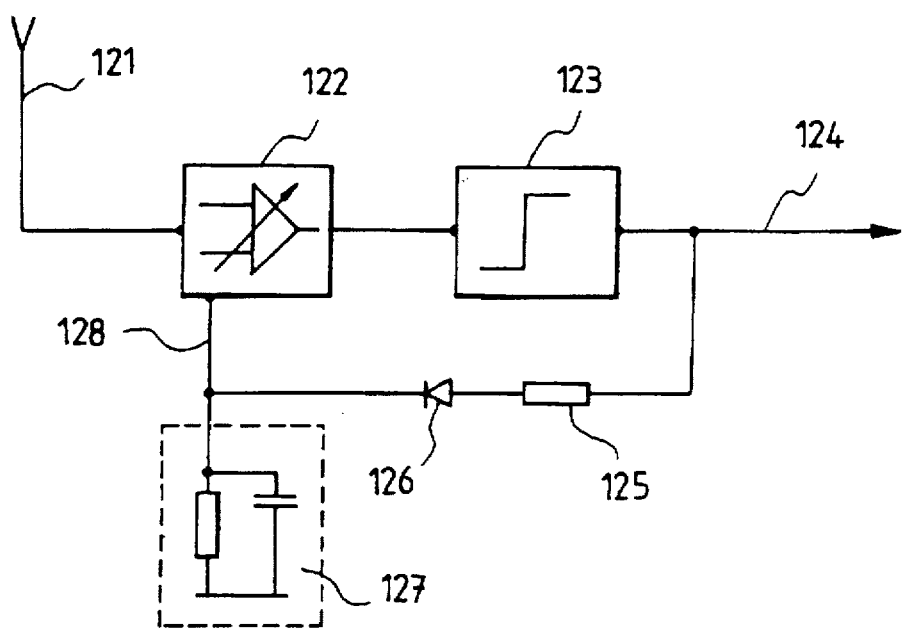

In the model illustrated in FIG. 21, in much the same way as the model illustrated in FIG. 20, the dynamic gas sensor signal travels along cable 121 through an adjustable amplifier (in this model) 122 before being fed into switch amplifier 123. The output signal for the switch amplifier 123 present in the output cable 124 travels through charge resistor 125 and diode 126 and thus charges a resistance capacitor circuit 127 switched after diode 126, so that regulated voltage occurs, which is fed into the adjustable amplifier 122 via connection cable 128, thus influencing the amplification of adjustable amplifier 122.

The switch amplifier 123 which is switched after adjustable amplifier 122 works with a fixed set switch threshold.

Figure 22:
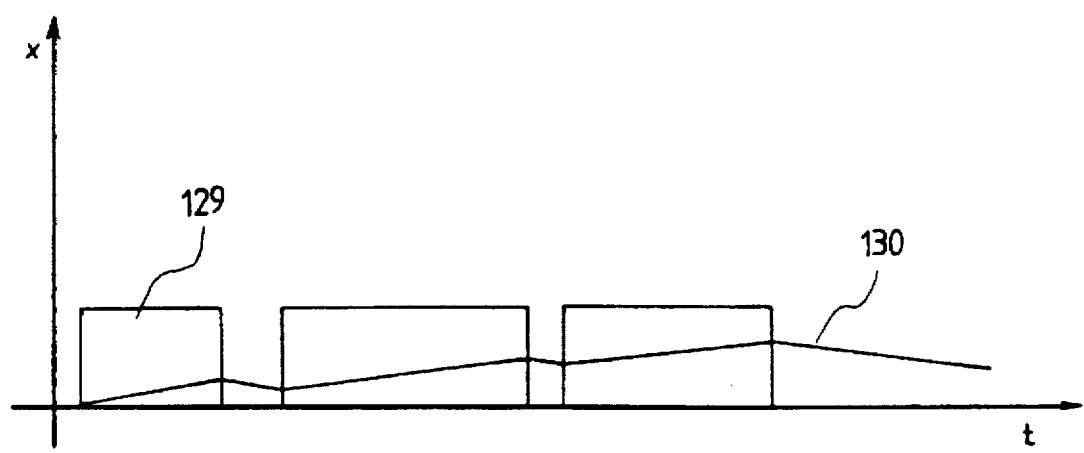
FIG. 22. A representation of load recognition line for a resistance capacitor circuit.

FIG. 22 shows how output signals 129 from the switch amplifier influence the charge curve 130 of the resistance capacitor circuit. It is clearly demonstrated that the charge current is a function of the frequency as well as of the duration of the switching of the output signal of the above-mentioned switch amplifier.

As already mentioned above, the evaluation unit with the circuits described above may be fitted as a centrally-programmed microprocessor, which works according to the above-listed switching criteria as a digital/numerical model.

Figure 23:
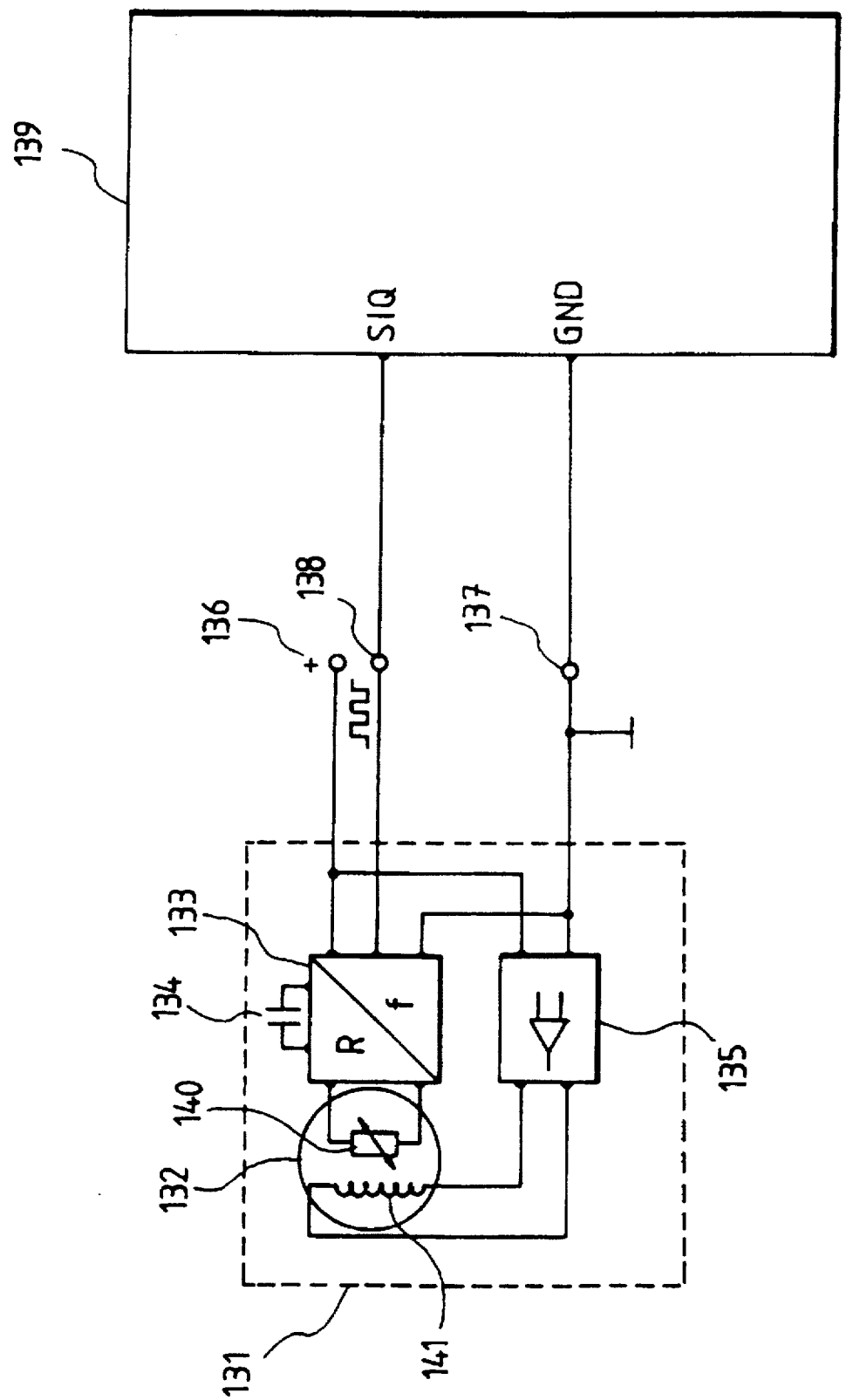
FIG. 23. The principles of a sensor module for the invented sensor system.

The model of the invented sensor system illustrated in FIG. 23 is the actual sensor part combined with the minimal amount of evaluation electronics necessary and fitted in a protective housing. The actual evaluation of data takes place in the microcomputer which is fitted in the heating and air-conditioning system of many vehicles already.

The model of the invented sensor system illustrated in FIG. 23 is fitted with a sensor module 131, a gas sensor element 132, oscillation circuit 133, a capacitor 134 which determines the frequency of oscillation circuit 133 and a heater control 135.

Gas sensor element 132 has an alterable (according to gas coating) ohmic resistor 140, connected to oscillation circuit 133, the frequency of which is determined by capacitor 134. By means of heater controller 135 the heater unit 141 of the gas sensor element 132 is adjusted.

Sensor module 131 is linked by means of electrical cables 136 and 137 to a voltage source, for example the central heating and ventilation system.

The gas sensor signal, altered through the oscillation circuit fitted as a Rf circuit, is fed into microcomputer 139 of the central heating and ventilation controller unit via cable 138.

We claim:

1. Sensor system to control ventilation systems in vehicles in recirculation or air input-mode dependent on the pollution levels in the air outside the vehicle, with a gas sensor element (52) the electrical resistance of which sinks in the presence of reducing gases and which rises in the presence of oxidizing gases, and an evaluation unit (51), the output of which is connected to the controller of the ventilation unit characterized by the fact that the sensor system is so organized that increase of a signal fed into the evaluation unit following an rise in the concentration of reducing gases is approximately quatitively equivalent to fall of the gas sensor signal fed into the evaluation unit (51) following a rise in the concentration of oxidizing gases, that the evaluation unit (51) calculates the rise or fall per time unit in the gas sensor signals which are fed into it and the evaluation unit (51) generates a switch signal to adjust the ventilation system to recirculation mode as soon as the measured increase or decrease in the gas sensor signal per time unit numerically exceeds a threshold limit.

2. Sensor system according to claim 1, under which a mean value (31) is calculated for a set time period from the gas sensor signal in the evaluation unit (51), this mean value (31) is allotted to a defined limit band (32) by proportional subtraction and addition of an absolute or by supplement or deduction based proportionally, and the switch signal is generated when the gas sensor signal lies outside this defined limit band (32).

3. Sensor system according to claims 1 or 2, under which the evaluation unit (51) has a band pass (57) which only allows an amplitude spectrum to pass, which displays the threshold limit-exceeding rise or fall of the gas sensor signal per time unit, through which gas sensor signal travels, in order to detect such a rise or fall of the gas sensor signal per time unit the output signal used to generate the switch signal for the control of the ventilation system has to be taken into account.

4. Sensor system according to claims 1 or 2, under which the evaluation unit (51) is equipped with a computer facility to enable the completion of a Fourier transformation, in which the gas sensor signal is arithmetically investigated for the presence of a certain rise or fall of the gas sensor signal per time unit displaying amplitude spectrum which exceeds a threshold limit, and in which the switch signal is generated in the evaluation unit in order to control the ventilation system, whenever such an amplitude spectrum is detected in the gas sensor signal.

5. Sensor system according to claims 1 or 2, under which the evaluation unit is fitted with a electronic neural network, in which the gas sensor signal is investigated for characteristics showing the presence of a threshold-excessive rise or fall in the gas sensor signal per time unit, and under which the switch signal is generated in the evaluation unit (51), if a rise or fall in the gas sensor signal which exceeds the threshold is detected in the cause of this investigation.

6. Sensor system according to claim 5, under which the electronic neural network takes the form of a triple or multiple-layer forwards-coupled neural network.

7. Sensor system according to claim 5, under which the electronic neural network takes the form of a triple or multiple-layer inverse-coupled neural network.

8. Sensor system according to claim 1 or 2, under which the evaluation unit (51) is fitted with an electronic FUZZY logic unit by means of which a rise or fall in the gas sensor signal per unit of time which exceeds the threshold value may be registered, and in which the switch signal is generated in the evaluation unit (51), if a rise or fall in the gas sensor signal per unit of time which exceeds the threshold is detected in the cause of this investigation.

9. Sensor system according to one of claims 1 to 2, in which the evaluation unit (51) is fitted with a storage unit, in which the peak points (40, 45) of the gas sensor signal are stored, and in which the switch signal is extinguished on the output side of the evaluation unit, if the gas sensor signal after the peak point (40, 45) shows a certain predeterminable signal level difference (42, 48) to the peak point (40, 45) and the gas sensor signal lies inside the band (32) allotted to the formed mean value (31).

10. Sensor system according to one of claims 1 to 2, in which the evaluation unit (51) is fitted with a controller unit to adjust the reactive sensitivity of the sensor system, by means of which the reactive sensitivity of the sensor system may be raised or lowered in case of rising or falling frequency of increases and decreases in gas sensor signal which exceed the threshold limit values, whereby the numerical degree of the alteration of the reactive sensitivity of the sensor system per unit of time is limited.

11. Sensor system according to claim 10, in which the controller unit used to adjust the reactive sensitivity of the sensor system is fitted with an external temperature sensor, which registers the air temperature outside the vehicle, an internal temperature sensor, which registers the air temperature inside the vehicle, and which has a comparative unit, which can compare the outside temperature provided by the external temperature sensor with the internal air temperature provided by the internal temperature sensor, whereby the controller unit raises or lowers the reactive sensitivity of the sensor system when the outside temperature is higher or lower than the inside temperature of the vehicle.

12. Sensor system according to one of claims 1 to 2, by which the evaluation unit (51) is fitted with a timer unit, by means of which the operating periods of the ventilation system in air input mode and in recirculation mode are measurable, a computer unit, by means of which the quotient of operating periods in air input mode and the operating periods of the ventilation system in recirculation mode is calculable, and is fitted with a controller, by means of which the reactive sensitivity of the sensor system may be reduced in case of increased recirculation mode operation, and increased in case of increased air input operation, whereby the degree of alteration of the reactive sensitivity per unit of time is limited.

13. Sensor system according to claim 12, in which the controller unit used to adjust the reactive sensitivity of the sensor system is fitted with an external temperature sensor, which registers the air temperature outside the vehicle, an internal temperature sensor, which registers the air temperature inside the vehicle, and which has a comparative unit, which can compare the outside temperature provided by the external temperature sensor with the internal air temperature provided by the internal temperature sensor, whereby the controller unit raises or lowers the reactive sensitivity of the sensor system when the outside temperature is higher or lower than the inside temperature of the vehicle.

14. Sensor system according to one of claims 1 to 2, in which the evaluation (51) unit, together with the controller for the ventilation system, is analog technically formed.

15. Sensor system according to one of the claims 1 to 2, in which the gas sensor element (52) takes the form of a mixed oxide sensor element, the gas-sensitive layer of which contains tin dioxide (SnO2), tungsten trioxide (WO3), ferric oxide (Fe2O3), aluminium oxide (Al2O3), with platinum (Pt) and palladium (Pd) as reaction accelerators.

16. Sensor system according to claim 15, in which the gas-sensitive layer of the mixed oxide sensor element (52) takes the form of a mixed oxide sensor element, containing 29% to 49% tin dioxide (SnO2), 28% to 48% tungsten trioxide (WO3), 7% to 13% ferric oxide (Fe2O3), 7% to 13% aluminium oxide (Al2O3), with 0.5% to 1.5% platinum (Pt) and 1% to 3% palladium (Pd).

17. Sensor system according to one of claims 1 to 2, in which the gas sensor element (52) is electrically contacted with precious metal wires, preferably platinum wires, and is mounted in a cut-out (75) within an electrical circuit board (66) to the evaluation unit (51) with approximately the same middle plane as the circuit board, and gas sensor element connections directly soldered to the circuit board (66), so that the gas sensor element (52) hangs freely.

18. Sensor system according to one of claims 1 to 2, in which the evaluation unit (51) is, together with the controller for the ventilation system, in the form of a centrally-programmed microprocessor.

19. Sensor system according to one of claims 1 to 2, in which the gas sensor element (52) is placed in a chamber (67) which is closed gas-tight to the evaluation unit (51) and has a low volume, together with stable, gas-permeable walls.

20. Sensor system according to claim 19, in which at least one layer (72) of the gas-permeable material is positioned between two layer (73, 74) of woven metal mesh.

21. Sensor system according to claim 20, in which at least one layer (72) of the gas-permeable material is made of plastic film.

22. Sensor system according to claim 19, in which at least one layer (72) of the gas-permeable material is made of plastic film.

23. Sensor system according to claim 22, in which the plastic film is made of Teflon or some similar material.

24. Sensor system according to claim 23, in which the stable formed and gas-permeable walls (68) of the chamber (67) housing the gas sensor element (52) is made of sintered plastic, glass, metal or some similar material.

25. Sensor system according to claim 19, in which at least one layer (72) of the gas-permeable material is bedded between two stable formed and perforated layers made of thermoplastic material.

26. Sensor system according to claim 25, in which at least one layer (72) of the gas-permeable material is made of plastic film.

27. Sensor system according to one of the claims 1 to 2, in which the ohmic resistor (140) for the gas sensor element (132) is part of an oscillation circuit (133) through which flows middle frequency a.c. voltage.

28. Sensor system according to claim 27, in which a capacitor (134) is fitted, which produces the frequency of the oscillation circuit (133).

29. Sensor system according to claim 28, in which the oscillation circuit (82) is fitted with a timer component (82), which is switched with a frequency fixing capacitor (85) and/has a feed-back branch (86), in which the resistor (87) of the gas sensor element (88) and a second resistor (90) are fitted, and which has a parallel branch to the resistor (87) of the gas sensor element (88), in which a third resistor (89) is fitted.

30. Sensor system according to claim 27, in which the oscillation circuit (82) is fitted with a timer component (82), which is switched with a frequency fixing capacitor (85) and has a feed-back branch (86), in which the resistor (87) of the gas sensor element (88) and a second resistor (90) are fitted, and which has a parallel branch to the resistor (87) of the gas sensor element (88), in which a third resistor (89) is fitted.

31. Sensor system according to claim 19, in which the walls (68) of the chamber (67) at least, partially consist of a perforated work material, which holds stably and mechanically supports at least one layer of a gas-permeable material.

32. Sensor system according to claim 31, in which at least one layer (72) of the gas-permeable material is bedded between two stable formed and perforated layers made of thermoplastic material.

33. Sensor system according to claim 32, in which at least one layer (72) of the gas-permeable material is made of plastic film.

34. Sensor system according to claim 31, in which at least one layer (72) of the gas-permeable material is made of plastic film.

35. Sensor system according to claim 31, in which at least one layer (72) of the gas-permeable material is positioned between two layer (73, 74) of woven metal mesh.

36. Sensor system according to claim 35, in which at least one layer (72) of the gas-permeable material is made of plastic film.

37. Sensor system according to one of claims 1 to 2, in which the gas sensor element (132) and a part unit (133, 134, 135) of the evaluation unit are brought together in a sensor module (131), the part unit (133, 134, 135) of the evaluation unit fitted with a oscillation circuit (133), a capacitor (134) to determine the frequency of the oscillation circuit (133) and a heater controller (135) to control the temperature of the gas sensor element (132), and the oscillation circuit (133) and the heater controller (135) are connected to a central heating and ventilation controlling device (139) for the vehicle, whereby the processing of an output signal from the sensor module (131) takes place completely digitally in the microcomputer of the central heating and ventilation controlling device (139).

38. Sensor system according to one of the claims 1 to 2, in which the gas sensor element made of metal oxide is kept at a constant temperature by means of a heating element (53).

39. Sensor system according to claim 38, in which the oscillation circuit (82) is fitted with a timer component (82), which is switched with a frequency fixing capacitor (85) and has a feed-back branch (86), in which the resistor (87) of the gas sensor element (88) and a second resistor (90) are fitted, and which has a parallel branch to the resistor (87) of the gas sensor element (88), in which a third resistor (89) is fitted.

* * * * *